United States Patent [19]

Hayashida et al.

[11] Patent Number: 5,112,961
[45] Date of Patent: May 12, 1992

[54] DNA ENCODING SUBUNITS OF A HIGH AFFINITY GM-CSF RECEPTOR

[75] Inventors: Kazuhiro Hayashida; Toshio Kitamura; Atsushi Miyajima, all of Palo Alto, Calif.

[73] Assignee: Schering Corporation, Kenilworth, N.J.

[21] Appl. No.: 554,745

[22] Filed: Jul. 18, 1990

[51] Int. Cl.⁵ .................. C07H 17/00; C12P 21/06; C07K 13/00; C07K 15/00
[52] U.S. Cl. .................................. 536/27; 435/69.1; 435/69.5; 530/350; 530/351
[58] Field of Search ..................... 536/27; 435/69.1

[56] References Cited

PUBLICATIONS

Gearing et al. (1989) Expression Cloning of a Receptor for Human Granulocyte-Macrophage CSF, EMBO 8, 3667-3676.

*Primary Examiner*—Elizabeth C. Weimar
*Assistant Examiner*—Deborah Crouch
*Attorney, Agent, or Firm*—Stephen C. Macevicz

[57] ABSTRACT

Nucleic acids encoding the β chain of the human granulocyte-macrophage colony stimulating factor (GM-CSF) receptor, as well as the β chain itself, are provided. The β chain may be expressed with the α chain in cellular hosts to form compositions useful in screening agonists and antagonists of human GM-CSF.

4 Claims, 11 Drawing Sheets

```
     GAAGACTGGT CTCTCCCACC ACACAGAGGC CTGGAGGAGG CAGAGGCCAG   50
     GAGGGAGAGG TCCCAAGAGC CTGTGAAATG GGTCTGGCCT GGCTCCCAGC  100
     TGGGCAGGAA CACAGGACTT CAGGACACTA AGGACCCTGT CATGCCCATG  150
     GCCCAGCACCC ACCAGTGCTG GTGCCTGCCT GTCCAGAGCT GACCAGGGAG  200

ATG GTG CTG GCC CAG GGG CTG CTC TCC ATG GCC CTG CTG GCC  242
  1  MET Val Leu Ala Gln Gly Leu Leu Ser Met Ala Leu Leu Ala

CTG TGC TGG GAG CGC AGC CTG CGC CTG GCA GAA ACC ATC      284
 15  Leu Cys Trp Glu Arg Ser Leu Arg Leu Ala Glu Thr Ile

CCG CTG CAG ACC CTG CGC TGC TAC AAC GAC TAC AGC CAC      326
 29  Pro Leu Gln Thr Leu Arg Cys Tyr Asn Asp Tyr Ser His

ATC ACC TGC AGG TGG GCA GAC ACC CAG GAT GCC CAG CGG CTC  368
 43  Ile Thr Cys Arg Trp Ala Asp Thr Gln Asp Ala Gln Arg Leu

GTC AAC GTG ACC CTC ATT CGC CGG GTG AAT GAG GAC CTC CTG  410
 57  Val Asn Val Thr Leu Ile Arg Arg Val Asn Glu Asp Leu Leu

GAG CCA GTG TCC TGT GAC CTC AGT GAT GAC ATG CCC TGG TCA  452
 71  Glu Pro Val Ser Cys Asp Leu Ser Asp Asp Met Pro Trp Ser

GCC TGC CCC CAT CCC CGC TGC GTG CCC AGG AGA TGT GTC ATT  494
 85  Ala Cys Pro His Pro Arg Cys Val Pro Arg Arg Cys Val Ile

CCC TGC CAG AGT TTT GTC GTC ACT GAC GTT GAC TAC TTC TCA  536
 99  Pro Cys Gln Ser Phe Val Val Thr Asp Val Asp Tyr Phe Ser

Figure 1 (part 1)
```

| | | | | | | | |
|---|---|---|---|---|---|---|---|
| 113 | TTC Phe | CAA Gln | CCA Pro | GAC Asp | AGG Arg | CCT Pro | CTG Leu | GGC Gly | ACC Thr | CGG Arg | CTC Leu | ACC Thr | GTC Val | ACT Thr | 578 |
| 127 | CTG Leu | ACC Thr | CAG Gln | CAT His | GTC Val | CAG Gln | CCT Pro | CCT Pro | GAG Glu | CCC Pro | AGG Arg | GAC Asp | CTG Leu | CAG Gln | 620 |
| 141 | ATC Ile | AGC Ser | ACC Thr | GAC Asp | CAG Gln | GAC Asp | CAC His | TTC Phe | CTG Leu | CTG Leu | ACC Thr | TGG Trp | AGT Ser | GTG Val | 662 |
| 155 | GCC Ala | CTT Leu | GGG Gly | AGT Ser | CCC Pro | CAG Gln | AGC Ser | CAC His | CAC His | TGG Trp | TTG Leu | TCC Ser | CCA Pro | GAT Asp | 704 |
| 169 | CTG Leu | GAG Glu | TTT Phe | GAG Glu | GTG Val | GTC Val | TAC Tyr | AAG Lys | CGG Arg | CTT Leu | CAG Gln | GAC Asp | TCT Ser | TGG Trp | 746 |
| 183 | GAG Glu | GAC Asp | GCA Ala | GCC Ala | ATC Ile | CTC Leu | CTC Leu | TCC Ser | AAC Asn | ACC Thr | TCC Ser | CAG Gln | GCC Ala | ACC Thr | 788 |
| 197 | CTG Leu | GGG Gly | CCA Pro | GAG Glu | CAC His | CTC Leu | ATG Met | CCC Pro | AGC Ser | ACC Thr | TAC Tyr | GTG Val | GCC Ala | 830 |
| 211 | CGA Arg | GTA Val | CGG Arg | ACC Thr | CGC Arg | CTG Leu | GCC Ala | CCA Pro | GGT Gly | TCT Ser | CGG Arg | CTC Leu | TCA Ser | GGA Gly | 872 |
| 225 | CGT Arg | CCC Pro | AGC Ser | AAG Lys | TGG Trp | AGC Ser | CCA Pro | GAG Glu | GTT Val | TGC Cys | TGG Trp | GAC Asp | TCC Ser | CAG Gln | 914 |

Figure 1 (part 2)

|     |     |     |     |     |     |     |     |     |     |      |
| --- | --- | --- | --- | --- | --- | --- | --- | --- | --- | ---- |
| 239 | CCA Pro | GGG Gly | GAT Asp | GAG Glu | GCC Ala | CAG Gln | CCC Pro | CAG Gln | AAC Asn | CTG Leu | GAG Glu | TGC Cys | TTC Phe | TTT Phe | 956 |
| 253 | GAC Asp | GGG Gly | GCC Ala | GCC Ala | GTG Val | CTC Leu | AGC Ser | TGC Cys | TCC Ser | TGG Trp | GAG Glu | GTG Val | AGG Arg | AAG Lys | 998 |
| 267 | GAG Glu | GTG Val | GCC Ala | AGC Ser | TCG Ser | GTC Val | TCC Ser | TTT Phe | GGC Gly | CTA Leu | TTC Phe | TAC Tyr | AAG Lys | CCC Pro | 1040 |
| 281 | AGC Ser | CCA Pro | GAT Asp | GCA Ala | GGG Gly | GAA Glu | GAG Glu | TGC Cys | TCC Ser | CCA Pro | GTG Val | CTG Leu | AGG Arg | 1082 |
| 295 | GAG Glu | GGG Gly | CTC Leu | GGC Gly | AGC Ser | CTC Leu | CAC His | ACC Thr | AGG Arg | CAC His | CAC His | TGC Cys | CAG Gln | ATT Ile | 1124 |
| 309 | CCC Pro | GTG Val | CCC Pro | GAC Asp | CCC Pro | GCG Ala | ACC Thr | GAG Glu | GGC Gly | CAA Gln | TAC Tyr | AAG Lys | AGC Ser | GTC Val | TCT Ser | 1166 |
| 323 | GTT Val | CAG Gln | CCA Pro | AGG Arg | AGG Arg | GCA Ala | GAG Glu | GCC Ala | ATA Ile | CAC His | AAA Lys | TCC Ser | ATC Ile | GTC Val | GTG Val | 1208 |
| 337 | AAC Asn | ATC Ile | CAG Gln | ATG Met | GCC Ala | CCT Pro | CCA Pro | TCC Ser | CTC Leu | AAC Asn | GTG Val | ACC Thr | AAG Lys | GAT Asp | 1250 |
| 351 | GGA Gly | GAC Asp | AGC Ser | TAC Tyr | AGC Ser | CTG Leu | CGC Arg | TGG Trp | GAA Glu | ACA Thr | ATG Met | AAA Lys | ATG Met | CGA Arg | 1292 |

Probe C underlined at row 323 (CCT) through row 337 (Asn Ile Gln Met Ala Pro ...)

Figure 1 (part 3)

| | | | | | | | | | | | | | | |
|---|---|---|---|---|---|---|---|---|---|---|---|---|---|---|
| 365 | TAC Tyr | GAA Glu | CAC His | ATA Ile | GAC Asp | CAC His | ACA Thr | TTT Phe | GAG Glu | ATC Ile | CAG Gln | TAC Tyr | AGG Arg | AAA 1334 Lys |
| 379 | GAC Asp | ACG Thr | GCC Ala | ACG Thr | TGG Trp | AAG Lys | GAC Asp | AGC Ser | AAG Lys | ACC Thr | GAG Glu | ACC Thr | CTC Leu | CAG 1376 Gln |
| 393 | AAC Asn | GCC Ala | CAC His | AGC Ser | ATG Met | GCC Ala | CTG Leu | CCA Pro | GCC Ala | CTG Leu | GAG Glu | CCC Pro | TCC Ser | ACC 1418 Thr |
| 407 | AGG Arg | TAC Tyr | TGG Trp | GCC Ala | GTG Val | AGG Arg | GTC Val | AGG Arg | TCC Ser | AGG Arg | ACC Thr | CGC Arg | ACC Thr | GGC 1460 Gly |
| 421 | TAC Tyr | AAC Asn | GGG Gly | ATC Ile | TGG Trp | AGC Ser | GAG Glu | TGG Trp | AGT Ser | GAG Glu | GCG Ala | CGC Arg | TCC Ser | TGG 1502 Trp |
| 435 | GAC Asp | ACC Thr | GAG Glu | TCG Ser | GTG Val | CTG Leu | CCT Pro | ATG Met | TGG Trp | GTG Val | CTG Leu | GCC Ala | CTC Leu | ATC 1544 Ile |
| 449 | GTG Val | ATC Ile | TTC Phe | CTC Leu | ACC Thr | ACT Thr | GCT Ala | GTG Val | CTC Leu | CTG Leu | GCC Ala | CTC Leu | CGC Arg | TTC 1586 Phe |
| 463 | TGT Cys | GGC Gly | ATC Ile | TAC Tyr | GGG Gly | TAC Tyr | AGG Arg | CGC Arg (Fspl) | AGA Arg | AAG Lys | TGG Trp | GAG Glu | GAG Glu | GAG 1628 Glu |
| 477 | AAG Lys | ATC Ile | CCC Pro | AAC Asn | CCC Pro | AGC Ser | AAG Lys | AGC Ser | CAC His | CTG Leu | TTC Phe | CAG Gln | AAC Asn | GGG 1670 Gly |

Figure 1 (part 4)

|  |  |  |  |  |  |  |  |  |  |  |  |  |  |
|---|---|---|---|---|---|---|---|---|---|---|---|---|---|
| 491 | AGC Ser | GCA Ala | GAG Glu | CTT Leu | TGG Trp | CCC Pro | CCA Pro | GGC Gly | AGC Ser | ATG Met | TCG Ser | GCC Ala | TTC Phe | ACT Thr | 1712 |
| 505 | AGC Ser | GGG Gly | AGT Ser | CCC Pro | CCA Pro | CAC His | CAG Gln | GGG Gly | CCG Pro | TGG Trp | GGC Gly | AGC Ser | CGC Arg | TTC Phe | 1754 |
| 519 | CCT Pro | GAG Glu | CTG Leu | GAG Glu | GGG Gly | GTG Val | TTC Phe | CCT Pro | GTA Val | GGA Gly | TTC Phe | GAC Asp | AGC Ser | 1796 |
| 533 | GAG Glu | GTG Val | TCA Ser | CCT Pro | CTC Leu | ACC Thr | ATA Ile | GAG Glu | GAC Asp | CCC Pro | AAG Lys | CAT His | GTC Val | TGT Cys | 1838 |
| 547 | GAT Asp | CCA Pro | CCA Pro | TCT Ser | GGG Gly | CCT Pro | GAC Asp | ACG Thr | ACT Thr | CCA Pro | GCT Ala | TCA Ser | $\overline{\text{GAT}}$ Asp | 1880 |
|  |  |  |  |  |  |  |  |  |  |  |  |  | BglII |  |
| 561 | CTA Leu | CCC Pro | ACA Thr | GAG Glu | CAG Gln | CCC Pro | CCC Pro | AGC Ser | CCC Pro | CAG Gln | CCA Pro | GGC Gly | CCG Pro | CCT Pro | 1922 |
| 575 | GCC Ala | GCC Ala | TCC Ser | CAC His | ACA Thr | CCT Pro | GAG Glu | AAA Lys | CAG Gln | GCT Ala | TCC Ser | AGC Ser | TTT Phe | GAC Asp | 1964 |
| 589 | TTC Phe | AAT Asn | GGG Gly | CCC Pro | TAC Tyr | CTG Leu | GGG Gly | CAG Gln | CCG Pro | CAC His | AGC Ser | CGC Arg | TCC Ser | CTA Leu | 2006 |
| 603 | CCT Pro | GAC Asp | ATC Ile | CTG Leu | GGC Gly | CCC Pro | CAG Gln | CCG Pro | GAG Glu | CCC Pro | CCA Pro | CAG Gln | GAG Glu | GGT Gly | GGG Gly | 2048 |

Figure 1 (part 5)

|     |     |     |     |     |     |     |     |     |     |     |     |      |
|-----|-----|-----|-----|-----|-----|-----|-----|-----|-----|-----|-----|------|
|     | AGC | CAG | AAG | TCC | CCA | CCT | GGG | TCC | CTG | GAG | TAC | CTG TGT 2090 |
| 617 | Ser | Gln | Lys | Ser | Pro | Pro | Gly | Ser | Leu | Glu | Tyr | Leu Cys |
|     |     |     | Probe B |   |     |     |     |     |     |     |     |      |
|     | CTG | CCT | GCT | GGG | GGG | CAG | GTG | CAA | CTG | GTC | CCT | CTG GCC CAG 2132 |
| 631 | Leu | Pro | Ala | Gly | Gly | Gln | Val | Gln | Leu | Val | Pro | Leu Ala Gln |
|     | GCG | ATG | GGA | CCG | GGA | CAG | GCC | GTG | GAA | GTG | GAG | AGA AGG CCG 2174 |
| 645 | Ala | Met | Gly | Pro | Gly | Gln | Ala | Val | Glu | Val | Glu | Arg Arg Pro |
|     | AGC | CAG | GGG | GCT | GCA | GGG | AGT | CCC | TCC | CTG | GAG | TCC GGG GGA 2216 |
| 659 | Ser | Gln | Gly | Ala | Ala | Gly | Ser | Pro | Ser | Leu | Glu | Ser Gly Gly |
|     | GGC | CCT | GCC | CCT | CCT | CTT | GCT | CTT | GGG | CCA | AGG | GTG GGA CAG 2258 |
| 673 | Gly | Pro | Ala | Pro | Pro | Leu | Ala | Leu | Gly | Pro | Arg | Val Gly Gln |
|     | GAC | CAA | AAG | GAC | AGC | CCT | GTG | GCT | ATA | CCC | ATG | AGC TCT GGG 2300 |
| 687 | Asp | Gln | Lys | Asp | Ser | Pro | Val | Ala | Ile | Pro | Met | Ser Ser Gly |
|     | GAC | ACT | GAG | GAC | CCT | GGA | GTG | GCC | TCT | GGT | TAT | GTC TCC TCT 2342 |
| 701 | Asp | Thr | Glu | Asp | Pro | Gly | Val | Ala | Ser | Gly | Tyr | Val Ser Ser |
|     | GCA | GAC | CTG | GTA | TTC | ACC | CCA | AAC | TCA | GTG | GCC | TCG TCT GTC 2384 |
| 715 | Ala | Asp | Leu | Val | Phe | Thr | Pro | Asn | Ser | Val | Ala | Ser Ser Val |
|     | TCC | CTA | GTT | CCC | TCT | CTG | GGC | CTC | CCC | TCA | GAC | CAG ACC CCC 2426 |
| 729 | Ser | Leu | Val | Pro | Ser | Leu | Gly | Leu | Pro | Ser | Asp | Gln Thr Pro |

Figure 1 (part 6)

```
743  AGC TTA TGT CCT GGG CTG GCC AGT GGA CCC CCT GGA GCC CCA 2468
     Ser Leu Cys Pro Gly Leu Ala Ser Gly Pro Pro Gly Ala Pro

757  GGC CCT GTG AAG TCA GGG TTT GAG GGC TAT GTG GAG CTC CCT 2510
     Gly Pro Val Lys Ser Gly Phe Glu Gly Tyr Val Glu Leu Pro

771  CCA ATT GAG GGC CGG TCC CCC AGG TCA CCA AGG AAC AAT CCT 2552
     Pro Ile Glu Gly Arg Ser Pro Arg Ser Pro Arg Asn Asn Pro

785  GTC CCC CCT GAG GCC AAA AGC GTC CTG AAC CCA GGG GAA 2594
     Val Pro Pro Glu Ala Lys Ser Pro Val Leu Asn Pro Gly Glu

799  CGC CCG GCA GAT GTG TCC CCA ACA TCC CAG CCC GAG GGC 2636
     Arg Pro Ala Asp Val Ser Pro Thr Ser Gln Pro Glu Gly Gly

813  CTC CTT GTC CAG CAA GTG GGC GAC TAT TGC TTC CTC CCC 2678
     Leu Leu Val Gln Gln Val Gly Asp Tyr Cys Phe Leu Pro

827  GGC CTG GGG CCC CCT CTC TCG CGG AGT AAA CCT TCT 2720
     Gly Leu Gly Pro Leu Ser Leu Ser Arg Ser Lys Pro Ser

841  TCC CCG GGA CCC GGT CCT GAG ATC AAG AAC CTA GAC CAG GCT 2762
     Ser Pro Gly Pro Gly Pro Glu Ile Lys Asn Leu Asp Gln Ala

855  TTT CAA GTC AAG AAG CCC CCA GGC CAG GCT GTG CCC CAG GTG 2404
     Phe Gln Val Lys Lys Pro Pro Gly Gln Ala Val Pro Gln Val
```

Figure 1 (part 7)

```
869  CCC GTC ATT CAG CTC TTC AAA GCC CTG AAG CAG GAC TAC   2846
     Pro Val Ile Gln Leu Phe Lys Ala Leu Lys Gln Asp Tyr

883  CTG TCT CTG CCC CCT TGG GAG GTC AAC AAG CCT GGG GAG GTG   2888
     Leu Ser Leu Pro Pro Trp Glu Val Asn Lys Pro Gly Glu Val

897  TGT TGA GACC CCCAGGCCTA GACAGGCAAG GGGATGGAGA GGGCTTGCCT   2938
     Cys ***

TCCCTCCCGC CTGACCTTCC TCAGTCATTT CTGCAAAGCC AAGGGGCAGC   2988
     CTCCTGTCAA GGTAGCTAGA GGCCTGGGAA AGGAGATAGC CTTGCTCCGG   3038
     CCCCCTTGAC CTTCAGCAAA TCACTTCTCT CCCTGCGCTC ACACAGACAC   3088
     ACACACACAC ACGTACATGC ACACATTTTT CCTGTCAGGT TAACTTATTT   3138
     GTAGGTTCTG CATTATTAGA ACTTTCTAGA TATACTCATT CCATCTCCCC   3188
     CTCATTTTTT TAATCAGGTT TCCTTGCTTT TGCCATTTTT CTTCCTTCTT   3238
     TTTTCACTGA TTTATTATGA GAGTGGGGCT GAGGTCTGAG CTGAGCC TTA   3288
     └─ Probe A
     TCAGACTGAG ATGCGGGCT GG TTGTGTTGAG GACTTGTGTG GGCTGCCTGT   3338
     CCCCGGCAGT CGCTGATGCA CATGACATGA TTCTCATCTG GGTGCAGAGG   3388
     TGGGAGGCAC CAGGTGGGCA CCCGTGGGGG TTAGGGCTTG GAAGAGTGGC   3438
     ACAGGACTGG GCACGCTCAG TGAGGCTCAG GGAATTC                 3475
```

Figure 1 (part 8)

DNA ENCODING SUBUNITS OF A HIGH AFFINITY GM-CSF RECEPTOR

FIELD OF THE INVENTION

The invention relates generally to the human granulocyte-macrophage colony stimulating factor (GM-CSF) receptor, and more particularly, to the synthesis of a human GM-CSF receptor component and to the use of the receptor component for screening agonists and antagonists of human GM-CSF.

BACKGROUND

Circulating blood cells are constantly replaced by newly developed cells. Replacement blood cells are formed in a process termed hematopoiesis which involves the production of at least eight mature blood cell types within two major lineages: (1) the myeloid lineage which includes red blood cells (erythrocytes), macrophages (monocytes), eosinophilic granulocytes, megakaryocytes (platelets), neutrophilic granulocytes, basophilic granulocytes (mast cells); and (2) the lymphoid lineage which includes T lymphocytes, and B lymphocytes, Burgess and Nicola, Growth Factors and Stem Cells (Academic Press, New York, 1983). Much of the control of blood cell formation is mediated by a group of interacting glycoproteins termed colony stimulating factors (CSFs). These glycoproteins are so named because of the in vivo and in vitro assays used to detect their presence. Techniques for the clonal culture of hematopoietic cells in semisolid culture medium have been especially important in the development of in vitro assays. In such cultures, individual progenitor cells (i.e., cells developmentally committed to a particular lineage, but still capable of proliferation) are able to proliferate to form a colony of maturing progeny in a manner which is believed to be essentially identical to the comparable process in vivo. The role of CSFs in hematopoiesis is the subject of many reviews, and is of great interest to clinical investigators that must treat blood diseases or deficiencies, e.g. Metcalf, The Hemopoietic Colony Stimulating Factors (Elsevier, N.Y., 1984); Clark and Kamen, Science, Vol. 236, pgs. 1229-1237 (1987); Sachs, Science, Vol. 238, pgs. 1374-1379 (1987); Dexter et al, eds., Colony Stimulating Factors (Dekker, N.Y., 1990); and Morstyn et al, Cancer Investigation, Vol. 7, pgs. 443-456 (1989).

CSFs are believed to play a role in the development and progression of myeloid leukemias, e.g. Metcalf, Hamatol. Bluttransfus, Vol. 31, pgs 16-25 (1987). Myeloid leukemias are clonal neoplasms of granulocyte-macrophage precursor cells, which fall into two major groups: chronic myeloid leukemia (CML) and acute myeloid leukemia (AML). CML is characterized by expansion in the marrow of the granulocyte-monocyte population at all stages of maturation with massive enlargement of hematopoietic populations in the spleen and blood. While chemotherapy is successful in reducing the excessive size of the leukemic cell populations conventional regimens have not succeeded in preventing terminal acute transformation (of progressively higher proportions of cells into immature or abnormal forms) or in extending the life spans of afflicted patients, Metcalf (cited above, 1984). AML is characterized by an accumulation of immature granulocyte-monocyte blast cells with often little or no evidence of maturing granulocyte-monocyte cells. The disease primarily involves the bone marrow, and spleen enlargement usually is only moderate. Total blood nucleated cells may or may not be elevated but ther is a high proportion of immature blast cells associated with relatively few mature cells. There is usually an associated anemia, thrombocytopenia and a relative absence in the marrow and peripheral blood of mature granulocytes and monocytes. Death usually results from uncontrollable hemorrhage or overwhelming infections, Metcalf (cited above, 1984).

It is believed that both forms of leukemia are driven by abnormal production of, or responsiveness to, colony stimulating factors, particularly GM-CSF. In particular, it has been shown that leukemic cells from some AML patients are capable of autonomous in vitro proliferation because they express GM-CSF constitutively, and that such autonomous proliferation can be inhibited by the addition of GM-CSF neutralizing antiserum; Young et al., Blood, Vol. 68, pgs. 1178-1181 (1986). It is believed that myeloid leukemias, in particular AML, may be treated by blocking the ability of GM-CSF to stimulate cell growth.

Recently, a low affinity receptor of human GM-CSF, referred to herein as the α chain, has been cloned and characterized, Gearing et al, EMBO J., Vol. 8, pgs. 3667-3676 (1989). The availability of a high affinity human GM-CSF receptor would provide a valuable tool for screening candidate GM-CSF agonists and antagonists.

SUMMARY OF THE INVENTION

The invention is directed to a component of the human GM-CSF receptor, referred to herein as the β chain of the human GM-CSF receptor, and to compositions thereof which bind with high affinity to human GM-CSF. The invention includes allelic and genetically engineered variants of the β chain receptor and nucleic acids encoding the β chain receptor and its allelic and genetically engineered variants. Preferably, the receptor component of the invention is selected from the group of polypeptides of the open reading frame defined by the following amino acid sequence:

Formula I

MVLAQGLLSMALLALCWERSLAGAEETIPLQTLRCYNDYTSHITCRWADT
QDAQRLVNVTLIRRVNEDLLEPVSCDLSDDMPWSACPHPRCVPRRCVIPC
QSFVVTDVDYFSFQPDRPLGTRLTVTLTQHVQPPEPRDLQISTDQDHFLLTW
SVALGSPQSHWLSPGDLEFEVVYKRLQDSWEDAAILLSNTSQATLGPEHLM
PSSTYVARVRTRLAPGSRLSGRPSKWSPEVCWDSQPGDEAQPQNLECFFDG
AAVLSCSWEVRKEVASSVSFGLFYKPSPDAGEEECSPVLREGLGSLHTRHH
CQIPVPDPATHGQYIVSVQPRRAEKHIKSSVNIQMAPPSLNVTKDGDSYSL
RWETMKMRYEHIDHTFEIQYRKDTATWKDSKTETLQNAHSMALPALEPST
RYWARVRVRTSRTGYNGIWSEWSEARSWDTESVLPMWVLALIVIFLTTA
VLLALRFCGIYGYRLRRKWEEKIPNPSKSHLFQNGSAELWPPGSMSAFTS
GSPPHQGPWGSRFPELEGVFPVGFGDSEVSPLTIEDPKHVCDPPSGPDTTPA
ASDLPTEQPPSPQPGPPAASHTPEKQASSFDFNGPYLGPPHSRSLPDILGQP
EPPQEGGSQKSPPPGSLEYLCLPAGGQVQLVPLAQAMGPGQAVEVERRPSQ

-continued

Formula I

GAAGSPSLESGGGPAPPALGPRVGGQDQKDSPVAIPMSSGDTEDPGVASGY
VSSADLVFTPNSGASSVSLVPSLGLPSDQTPSLCPGLASGPPGAPGPVKSGF
EGYVELPPIEGRSPRSPRNNPVPPEAKSPVLNPGERPADVSPTSPQPEGLL
VLQQVGDYCFLPGLGPGPLSLRSKPSSPGPGPEIKNLDQAFQVKKPPGQAV
PQVPVIQLFKALKQQDYLSLPPWEVNKPGEVC wherein the standard single-letter notation is used to designate L-amino acids, e.g. Cohn, Meth. Enzymol., Vol. 106, pg 4 (1984). Most preferably, the receptor component of the invention is defined by the amino acid sequence:

Formula II

ERSLAGAEETIPLQTLRCYNDYTSHITCRWADTQDAQRLVNVTLIRRVNED
LLEPVSCDLSDDMPWSACPHPRCVPRRCVIPCQSFVVTDVDYFSFQPDRPL
GTRLTVTLTQHVQPPEPRDLQISTDQDHPLLTWSVALGSPQSHNLSFGDLEF
EVVYKRLQDSWEDAAILLSNTSQATLGPEHLMPSSTYVARVRTRLAPGSR
LSGRPSKWSPEVCWDSQPGDEAQPQNLECFFDGAAVLSCSWEVRKEVASSV
SFGLFYKPSPDAGEEECSPVLREGLGSLHTRHHCQIPVPDPATHGQYIVSVQ
PRRAEKHIKSSVNIQMAPPSLNVTKDGDSYSLRWETMKMRYEHIDHTFEI
QYRKDTATWKDSKTETLQNAHSMALPALEPSTRYWARVRVRTSRTGYNG
IWSEWSEARSWDTESVLPMWVLALIVIFLTTAVLLALRFCGIYGYRLRRK
WEEKIPNPSKSHLFQNGSAELWPPGSMSAFTSGSPPHQGPWGSRFPELEGV
FPVGFGDSEVSPLTIEDPKHVCDPPSGPDTTPAASDLPTEQPPSPQPGPPAAS
HTPEKQASSFDFNGPYLGPPHSRSLPDILGQPEPPQEGGSQKSPPPGSLEYLC
LPAGGQVQLVPLAQAMGPGQAVEVERRPSQGAAGSPSLESGGGPAPPALG
PRVGGQDQKDSPVAIPMSSGDTEDPGVASGYVSSADLVFTPNSGASSVSLV
PSLGLPSDQTPSLCPGLASGPPGAPGPVKSGFEGYVELPPIEGRSPRSPRNN
PVPPEAKSPVLNPGERPADVSPTSPQPEGLLVLQQVGDYCFLPGLGPGPLS
LRSKPSSPGPGPEIKNLDQAFQVKKPPGQAVPQVPVIQLFKALKQQDYLSL
PPWEVNKPGEVC

Although Formulas I and II include the intracellular domain of the β chain of the receptor, it is clear that truncated forms of the above sequences which retain their extracellular and transmembrane domains and their ability of operably associate with the α chain fall within the concept of the invention.

The invention is based in part on the discovery and cloning of cDNAs which are capable of expressing proteins that bind to human GM-CSF with high affinity. One such clone, designated pKH97, has been deposited with the American Type Culture Collection (ATCC) (Rockville, MD) under accession number 40847. The invention includes nucleic acids (i) that are effectively homologous to the cDNA insert of pKH97, and (ii) that encode proteins that form high affinity GM-CSF receptors in association with the low affinity α chain receptor protein, e.g. as encoded by pKH125, also deposited with the ATCC under accession number 40848. As used herein, high affinity in reference to GM-CSF receptor binding means that GM-CSF binds to the associated α and β chains of the receptor with a binding constant that is at least an order of magnitude less than that for binding to either component alone. More preferably, high affinity means that GM-CSF binds to the associated α and β chains of the receptor with a binding constant, $K_d$, less than 1 nM; and most preferably, less than 200 pM.

DETAILED DESCRIPTION OF THE INVENTION

I. Obtaining and Expressing cDNAs for the Human GM-CSF Receptor β Chain

The term "effectively homologous" as used herein means that the nucleotide sequence is capable of being detected by a hybridization probe derived from a cDNA clone of the invention. The exact numerical measure of homology necessary to detect nucleic acids coding for a receptor β chain depends on several factors including (1) the homology of the probe to non-β chain coding sequences associated with the target nucleic acids, (2) the stringency of the hybridization conditions, (3) whether single stranded or double stranded probes are employed, (4) whether RNA or DNA probes are employed, (5) the measures taken to reduce nonspecific binding of the probe, (6) the nature of the method used to label the probe, (7) the fraction of guanidine and cytosine bases in the probe, (8) the distribution of mismatches between probe and target, (9) the size of the probe, and the like. Preferably, an effectively homologous nucleic acid sequence is at least seventy percent (70%) homologous to the cDNA of the invention. More preferably, an effectively homologous nucleic acid is at least ninety percent (90%) homologous to the cDNA of the invention. Most particularly, an effectively homologous nucleic acid sequence is one whose cDNA can be isolated by a probe based on the nucleic acid sequence of FIG. 1 using a standard hybridization protocol with no more than a few false positive signals, e.g. less than a hundred. There is an extensive literature that provides guidance in selecting conditions for such hybridizations, e.g. Hames et al, Nucleic Acid Hybridization: A Practical Approach (IRL Press, Washington, D.C., 1985); Gray et al, Proc. Natl. Acad. Sci., Vol. 80, pgs. 5842-5846 (1983); Kafatos et al, Nucleic Acids Research, Vol. 7, pgs. 1541-1552 (1979); and Williams, Genetic Engineering, Vol. 1, pgs. 1-59 (1981), to name a few. By way of example, the nucleic acid of FIG. 1 can be used as a probe in colony hybridization assays as described by Benton and Davis, Science, Vol. 196, pg. 180 (1977). Preferably, low stringency conditions are employed for the probe employed (dissociation temperature depends on probe length). For example, for a probe of about 20-40 bases a typical prehybridization, hybridization, and wash protocol is as follows: (1) prehybridization: incubate nitrocellulose filters containing the denatured target DNA for 3-4 hours at 55° C. in $5\times$ Denhardt's solution, $5\times$ SSPE ($20\times$ SSPE consists of 174 g NaCl, 27,6 g $NaH_2PO_4$—$H_2O$, and 7.4 g EDTA in 800 ml $H_2O$ adjusted to pH 7.4 with 10N NaOH), 0.1% SDS, and 100 μg/ml denatured salmon sperm DNA, (2) hybridization: incubate filters in prehybridization solution plus probe at 55° C. for 2 hours, (3) wash: three 15 minute washes in 300-500 ml volumes of $6\times$ SSC and 0.1% SDS at room temperature, followed by a final 1-1.5 minute wash in 300-500 ml of $1\times$ SSC and 0.1% SDS at 55° C. Other equivalent procedures, e.g. employing organic solvents such as formamide, are well known in the art.

Homology as the term is used herein is a measure of similarity between two nucleotide (or amino acid) sequences. Homology is expressed as the fraction or percentage of matching bases (or amino acids) after two sequences (possibly of unequal length) have been aligned. The term alignment is used in the sense defined by Sankoff and Kruskal in chapter one of Time Warps, String Edits, and Macromolecules: The Theory and Practice of Sequence Comparison (Addison-Wesley, Reading, MA, 1983). Roughly, two sequences are aligned by maximizing the number of matching bases (or amino acids) between the two sequences with the insertion of a minimal number of "blank" or "null" bases into either sequence to bring about the maximum overlap. Given two sequences, algorithms are available for computing their homology, e.g. Needleham and Wunsch, J. Mol. Biol., Vol. 48, pgs. 443-453 (1970); and Sankoff and Kruskal (cited above) pgs. 23-29. Also, commercial services and software packages are available for performing such comparisons, e.g. Intelligenetics, Inc. (Mountain View, CA); and University of Wisconsin Genetics Computer Group (Madison, Wis.).

Figure 1:
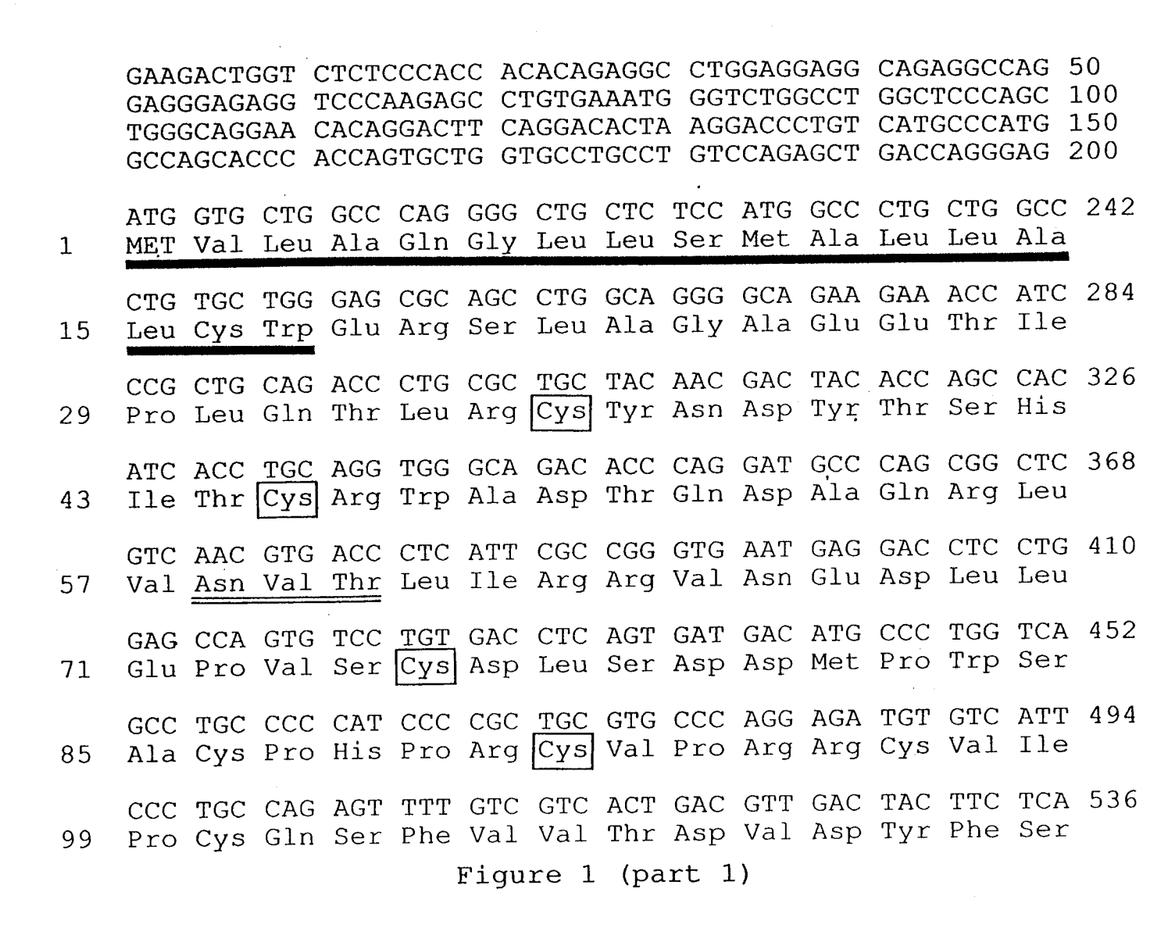
FIG. 1 lists the nucleotide sequence and deduced amino acid sequence of the human GM-CSF receptor component encoded by KH97. Numbers at the right and left margins indicate nucleotides and amino acids, respectively. The signal sequence and the transmembrane domain are marked by bars. Potential N-linked glycosylation sites in the extracellular domain are indicated by double underlines.

Probes based on the nucleic acid sequence of FIG. 1 can be synthesized on commercially available DNA synthesizers, e.g. Applied Biosystems model 381A, using standard techniques, e.g. Gait, Oligonucleotide Synthesis: A Practical Approach, (IRL Press, Washington D.C., 1984). It is preferable that the probe be at least 18-30 bases long. More preferably, the probe is at least 100-200 bases long. Probes of the invention can be labeled in a variety of ways standard in the art, e.g. radioactive labels, Berent et al, Biotechniques, pgs. 208-220 (May/June 1985), Meinkoth et al, Anal. Biochem., Vol. 138, pgs. 267-284 (1984), Szostak et al, Meth. Enzymol., Vol. 68, pgs. 419-429 (1979), and the like, and non-radioactive labels, Chu et al, DNA, Vol. 4, pgs. 327-331 (1985), Jablonski et al, Nucleic Acids Research, Vol. 14, pgs. 6115-6128 (1986), and the like.

Hybridization probes can also be used to screen candidate sources of $\beta$ chain mRNA prior to library construction, e.g. by RNA blotting, Maniatis et al, Molecular Cloning: A Laboratory Manual, pgs. 202-203 (Cold Spring Harbor Laboratory, N.Y., 1982); or Hames and Higgins, eds., pgs. 139-143 in Nucleic Acids Hybridization (IRL Press, Washington D.C., 1985). Sources of mRNA encoding the desired polypeptides include cell populations or cell lines that express, or can be induced to express, large numbers of GM-CSF receptors on their surfaces, e.g. in excess of 3-5000.

Preferably, the $\alpha$ and $\beta$ chains of the GM-CSF receptor are co-transfected into a mammalian expression system (i.e. host-expression vector combination). Many reviews are available which provide guidance for making choices and/or modifications of specific mammalian expression systems, e.g. to name a few, Kucherlapati et al., Critical Reviews in Biochemistry, Vol. 16, Issue 4, pgs. 349-379 (1984), and Banerji et al., Genetic Engineering, Vol. 5, pgs. 19-31 (1983) review methods for transfecting and transforming mammalian cells; Reznikoff and Gold, eds., Maximizing Gene Expression (Butterworths, Boston, 1986) review selected topics in gene expression in *E. coli*, yeast, and mammalian cells; and Thilly, Mammalian Cell Technology (Butterworths, Boston, 1986) reviews mammalian expression systems. Likewise, many reviews are available which describe techniques and conditions for linking and/or manipulating specific cDNAs and expression control sequences to create and/or modify expression vectors suitable for use with the present invention, e.g. Maniatis et al., Molecular Cloning: A Laboratory Manual (Cold Spring Harbor Laboratory, N.Y., 1982); Glover, DNA Cloning: A Practical Approach, Vol. I and II (IRL Press, Oxford, 1985), and Perbal, A Practical Guide to Molecular Cloning (John Wiley & Sons, N.Y. 1984), to name only a few.

Several DNA tumor viruses have been used as vectors for mammalian hosts. Particularly important are the numerous vectors which comprise SV40 replication, transcription, and/or translation control sequences coupled to bacterial replication control sequences, e.g. the pcD vectors developed by Okayama and Berg, disclosed in Mol. Cell. Biol., Vol. 2, pgs. 161-170 (1982) and Mol. Cell. Biol., Vol. 3, pgs. 280-289 (1983), both of which are incorporated herein by reference; the SV40 vectors disclosed by Hamer in Genetic Engineering, Vol. 2, pgs. 83-100 (1980), and U.S. Pat. No. 4,599,308, both of which are incorporated herein by reference; and the vectors additionally containing adenovirus regulatory elements, disclosed by Kaufman and Sharp, in Mol. Cell. Biol., Vol. 2, pgs. 1304-1319 (1982), and Clark et al., in U.S. Pat. No. 4,675,285, both of which are incorporated herein by reference. COS7 monkey cells, described by Gluzman, Cell, Vol. 23, pgs. 175-182 (1981) and available from the ATCC (accession no. CRL 1651), are usually the preferred hosts for the above vectors. SV40-based vectors suitable for mammalian receptor expression have been developed by Aruffo and Seed, Proc. Natl. Acad. Sci., Vol. 84, pgs. 3365-3369 and 8573-8577 (1987).

II. Binding Assays

Binding assays are accomplished by letting a ligand of unknown specificity or affinity compete with a known amount or concentration of labeled human GM-CSF for receptor binding sites of a sample of cells transfected or transformed with pKH97 and pKH125, or their equivalents. Preferably, the GM-CSF is labeled by radioiodianation using standard protocols, e.g. reaction with 1,3,4,6-tetrachloro-3α,6α-diphenylglycouril described by Fraker et al, Biochem Biophys. Res. Commun., Vol. 80, pgs. 849–857 (1978)(and available from Pierce Chemical Co. as Iodogen). Generally, the binding assay is conducted as described by Lowenthal et al, J. Immunol., Vol 140, pgs. 456–464 (1988), which is incorporated by reference. Briefly, aliquots of cells are incubated in the presence of $^{125}$I-labeled human GM-CSF in a final volume of 200 μl culture medium in microfuge tubes at 4° C. Cell-bound $^{125}$I-labeled GM-CSF was separated from non-bound $^{125}$I-labeled GM-CSF by centrifugation through an oil gradient (10,000×G for 2 min). Nonspecific binding is measured in the presence of a 100-fold excess of partially purified unlabeled human GM-CSF.

EXAMPLES

Example I. Construction of cDNA library from TF-1 cells and isolation of pKH97 and pKH125

Poly(A)+ RNA isolated from TF-1 cells (Kitamura et al, J. Cell. Physiol., Vol. 140, pgs. 323–334 (1989)) by the guanidium isothianate method (Chirgwin et al, Biochemistry, Vol. 18, pgs. 5294–5299 (1978)) was converted to double-stranded cDNA using oligo(dT) primers. After Bst XI linkers were ligated to both ends of the cDNAs, the cDNAs were digested with Xba I (the 3' region fortuitously containing a unique Xba I site) and re-cloned into Bst XI/Xba I-digested pME18, an SV40-based mammalian expression vector (see FIG. 3). pKH97 was isolated by using probes constructed from initially isolated truncated cDNAs. The trucated cDNAs were isolated using a $^{32}$P-labeled mouse interleukin-3 receptor cDNA fragment (described in Itoh et al, Science, Vol. 247, pgs. 324–334 (1990)) as a hybridization probe under low stringency conditions (hybridization at 42° C. with 6xSSPE in the presence of 20% formamide and washing at 50° C. with 2xSSPE). pKH97 was transfected into COS 7 cell by a standard protocol, e.g. as described by Yokota et al, Proc. Natl. Acad. Sci., Vol. 84, pgs. 7388–7392 (1987) (5 μg of plasmid DNA were transfected into semi-confluent COS 7 cells by the DEAE-dextran method; 72 hours after transfection, the cells were harvested for binding assays, using iodinated cytokines as described below). No specific binding was displayed by any of the following human cytokines at the following concentrations: IL-2 (1 nM), IL-3 (20 nM), IL-4 (1 nM), IL-5 (5 nM), GM-CSF (20 nM), and EPO (10 nM).

A cDNA encoding the α chain of the human GM-CSF receptor was isolated from the same library using the polymerase chain reaction with specific oligonucleotide primers corresponding to the 5'-untranslated and the 3'-untranslated regions of the cDNA described by Gearing et al, EMBO J., Vol. 8, pgs. 3667–3676 (1989). The isolated cDNA was inserted into pME18 to give pKH125.

Example II. Co-transfection of pKH97 and pKH125 into COS 7

A total of 5 μg of equal amounts of pKH97 and pKH125 plasmid DNA was transfected into semi-confluent COS 7 cells by the DEAE-dextran method. 72 hours after transfection, the cells were harvested and analyzed in GM-CSF binding assays. Duplicates of 2×10$^5$ COS 7 cells in 0.1 ml of RPMI 1640 containing 10% fetal calf serum, 2 mM EDTA, 0.02% sodium azide and 20 mM Hepes (pH 7.4) were incubated for 3 h at 4° C. with various concentrations of $^{125}$I-labeled human GM-CSF with or without an excess amount of non-labeled human GM-CSF. The cell-bound radioactivity was measured by separating the cells from free ligand by centrifugation through an oil layer, as described by Schreurs et al, Growth Factors, Vol. 2, pgs. 221–233 (1990). GM-CSF was iodinated by a standard protocol, Chiba et al, Leukemia, Vol. 4, pgs. 22–36 (1990). Briefly, 5 μg of E. coli-produced human GM-CSF was incubated in 30–50 μl of 50 mM sodium borate buffer (pH 8.0) with 1 mCi of the dried Bolton and Hunter reagent for 12–16 h at 4° C. Glycine was added to 2.5 mg/ml to stop the reaction and the iodinated GM-CSF was separated from the free Bolton and Hunter reagent by a PD-10 column. The iodinated human GM-CSF had a specific radioactivity of 4–8×10$^7$ cpm/μg and was stable for about two months in Hepes-buffered Hank's balanced salt solution containing 0.1% gelatin, 0.1% bovine serum albumin, and 0.02% sodium azide.

Figure 2A:
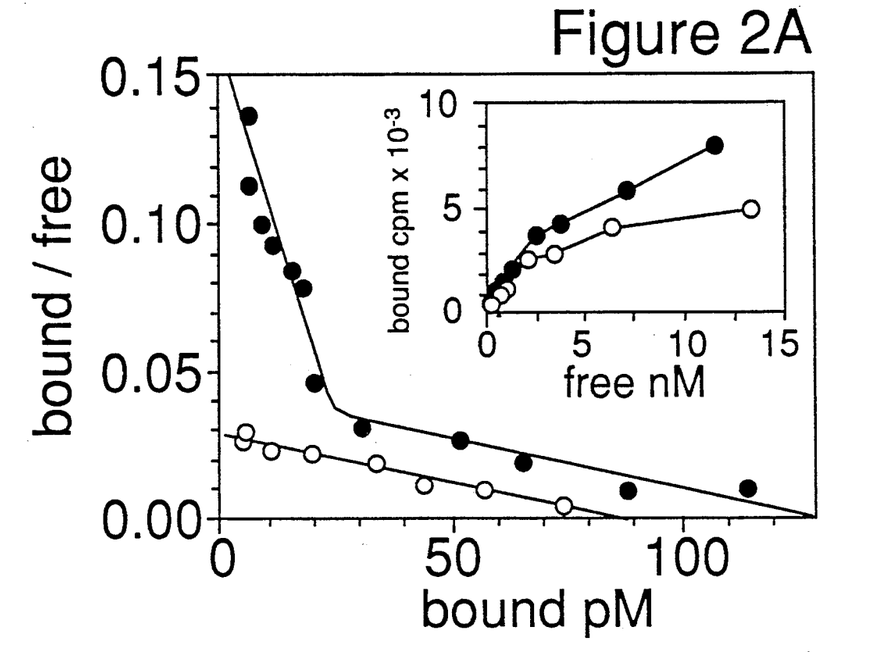
FIG. 2A illustrates the binding of $^{125}$I-labeled human GM-CSF to COS 7 cells transiently co-transfected with KH97 and pKH125.

FIG. 2A shows the receptor binding data. Open circles correspond COS 7 cells (controls) transfected with pKH125 and pME18 (same vector as pKH97, but without the cDNA insert). Closed circles correspond to COS 7 cells transfected with pKH125 and pKH97. The Scatchard plots of the binding data are shown. The inserted graphs show equilibrium binding profiles. As can be seen from the data both high ($K_d$=120 pM) and low ($K_d$=6.6 nM) affinity binding sites are indicated (the $K_d$ values being computed by the LIGAND program, De Lean et al, Mol. Pharmacol., Vol. 21, pgs. 5–16 (1982)).

Example III. Co-transfection of pKH97 and pKH125 into NIH3T3 Cells

Figure 2B:
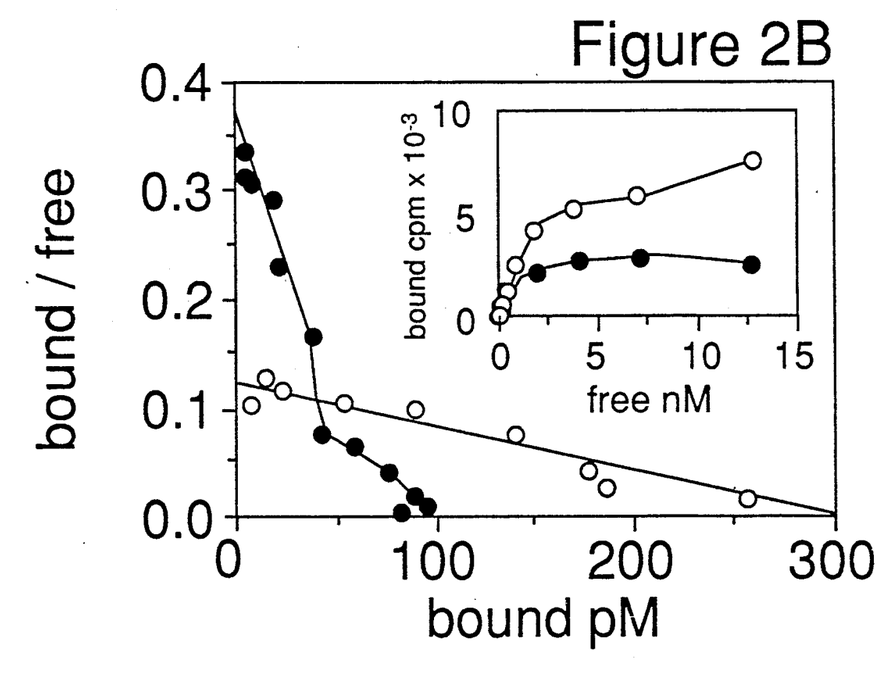
FIG. 2B illustrates the binding of $^{125}$I-labeled human GM-CSF to NIH3T3 cells stably transfected with KH97 and pKH125.
Figure 3A:
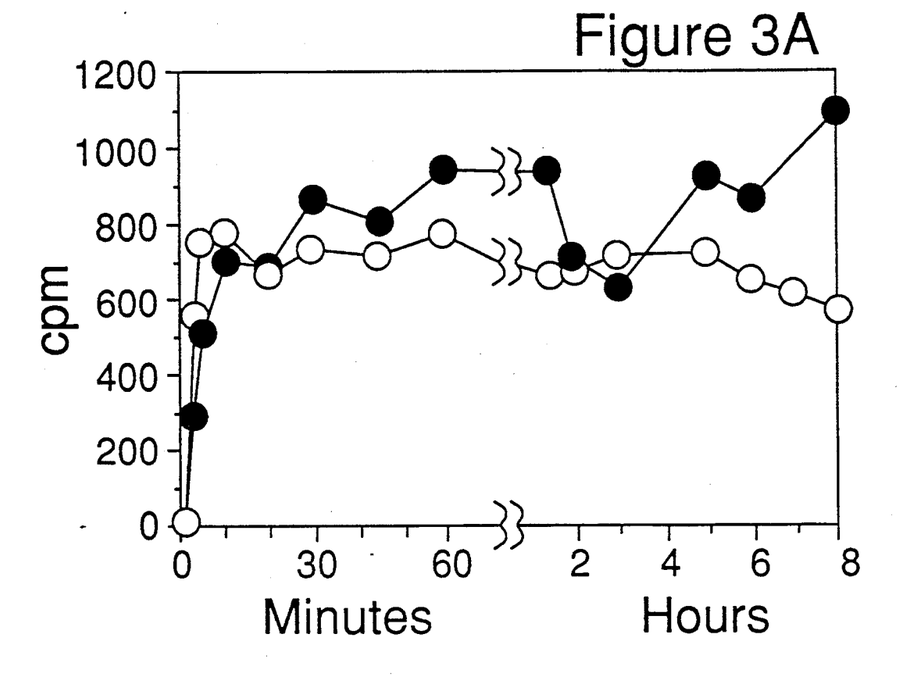
FIG. 3A illustrates the association rate of $^{125}$I-labeled human GM-CSF to the NIH3T3 stable transfectants.
Figure 3B:
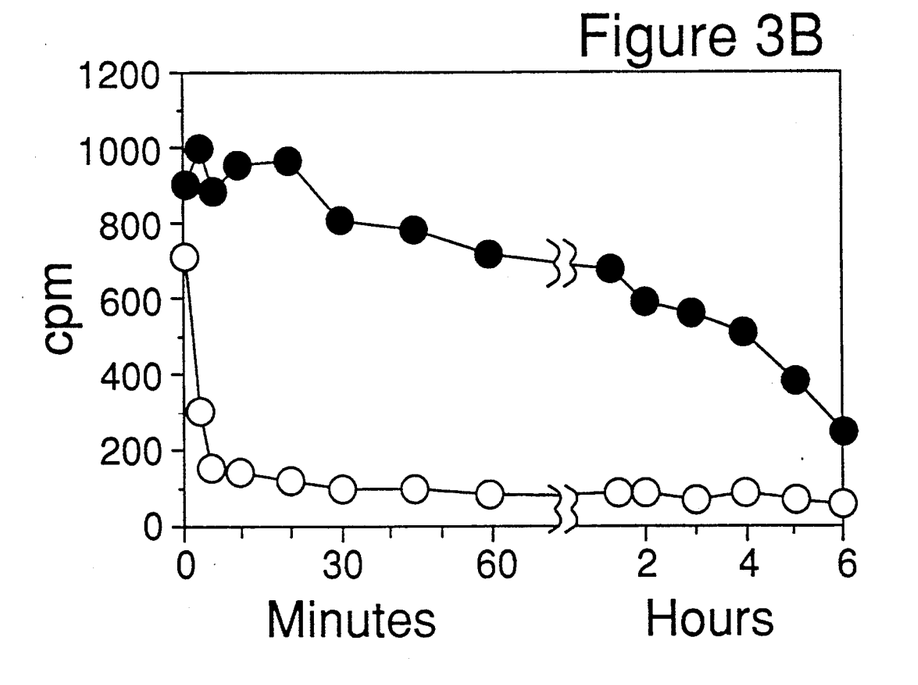
FIG. 3B illustrates the dissociation rate of $^{125}$I-labeled human GM-CSF to the NIH3T3 stable transfectants.
Figure 4:
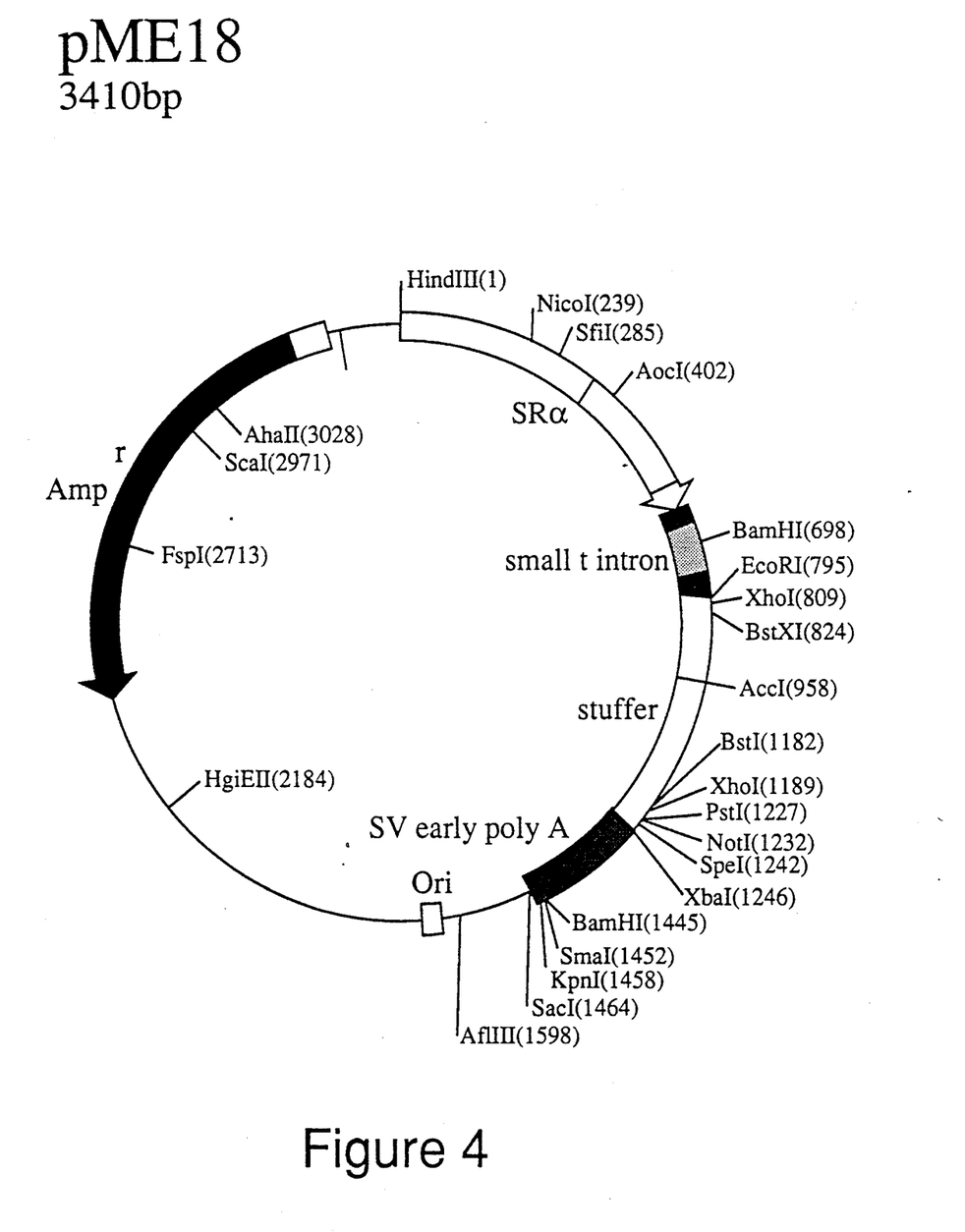
FIG. 4 is a restriction map of the vector pME18.

A DNA fragment containing the neomycin-resistance gene, neo, was inserted into pKH97 to form pKH97neo. NIH3T3 cells were stably transfected with pKH97neo and pKH125 by the calcium-phosphate procedure, described by Chen and Okayama, Mol. Cell. Biol., Vol. 7, pgs. 2745–2752 (1987), which reference is incorporated by reference. Stable transfectants were selected by 1 mg/ml of G418. FIG. 2B shows the binding data for the transfected NIH3T3 cells. As above, the open circles correspond to to control NIH3T3 cells transfected with pKH97neo and pME18. Closed circles correspond to NIH3T3 cells transfected with pKH97neo and pKH125. The latter displayed high affinity binding with a $K_d$ of 170 pM. Labeled GM-CSF association and dissociation rates were also examined in the transfected NIH3T3 cells. FIGS. 3A and 3B illustrates the data. Open circles correspond to NIH3T3 cells expressing only the α chain. Closed circles correspond to NIH3T3 cells expressing both the α chain and β chain of the GM-CSF receptor. The latter displayed a much slower rate of dissociation ($T_{\frac{1}{2}}$=2 min versus $T_{\frac{1}{2}}$=360 min).

Example IV. Use of Co-transfected COS 7 cells to screen for GM-CSF Antagonists Aliquots of COS 7 cells co-transfected with pKH97 and pKH125 as described above are distributed to wells of microtiter plates in 200 μl of medium containing $^{125}$I-labeled human GM-CSF at concentrations of 100 pM, 500 pM, and 1 nM. 100 μl samples of microbial supernatants free of cells are added to the transfected COS 7 cells at each of the different concentrations of $^{125}$I-labeled GM-CSF. After incubating for 3 hours the COS 7 cells are harvested and assayed for bound radioactivity. COS 7 cells with low counts of bound radioactivity correspond microbial samples containing candidate antagonists or agonists of human GM-CSF.

The descriptions of the foregoing embodiments of the invention have been presented for purpose of illustration and description. They are not intended to be exhaustive or to limit the invention to the precise forms disclosed, and obviously many modifications and variations are possible in light of the above teaching. The embodiments were chosen and described in order to best explain the principles of the invention to thereby enable others skilled in the art to best utilize the invention in various embodiments and with various modifications as are suited to the particular use contemplated. It is intended that the scope of the invention be defined by the claims appended hereto.

Applicants have deposited pKH97 and pKH125 with the American Type Culture Collection, Rockville, MD, USA (ATCC), under accession numbers 40847 and 40848, respectively. These deposits were made under conditions as provided under ATCC's agreement for Culture Deposit for Patent Purposes, which assures that the deposit will be made available to the US Commissioner of Patents and Trademarks pursuant to 35 USC 122 and 37 CFR 1.14, and will be made available to the public upon issue of a U.S. patent, which requires that the deposit be maintained. Availability of the deposited plasmids is not to be construed as a license to practice the invention in contravention of the rights granted under the authority of any government in accordance with its patent laws.

We claim:

1. An isolated and purified nucleic acid as shown in FIG. 1 which encodes a polypeptide capable of forming a high affinity receptor having a binding constant less than 200 pM for human granulocyte-macrophage colony stimulating factor when operably associated with the α chain of a human granulocyte-macrophage colony stimulating factor receptor and an isolated and purified nucleic acid sequence which hybridizes to the nucleic acid sequence shown in FIG. 1 and which encodes a polypeptide capable of forming a high affinity receptor having a binding constant less than 200 pM for human granulocyte macrophage colony stimulating factor when operably associated with the α chain of a human granulocyte-macrophage colony stimulating factor receptor.

2. The nucleic acid of claim 1 wherein said polypeptide forms said high affinity receptor with said α chain in a mammalian expression host co-transfected with a vector carrying the nucleic acid and a vector carrying DVA encoding α chain.

3. A nucleic acid capable of encoding a polypeptide of an open reading frame defined by the amino acid sequence:

MVLAQGLLSMALLALCWERSLAGAEETIPLQTLRCYNDYTSHITCRWADT
QDAQRLVNVTLIRRVNEDLLEPVSCDLSDDMPWSACPHPRCVPRRCVIPC
QSFVVTDVDYFSFQPDRPLGTRLTVTLTQHVQPPEPRDLQISTDQDHFLLTW
SVALGSPQSHWLSPGDLEFEVVYKRLQDSWEDAAILLSNTSQATLGPEHLM
PSSTYVARVRTRLAPGSRLSGRPSKWSPEVCWDSQPGDEAQPQNLECFFDG
AAVLSCSWEVRKEVASSVSFGLFYKPSPDAGEEECSPVLREGLGSLHTRHH
CQIPVPDPATHGQYIVSVQPRRAEKHIKSSVNIQMAPPSLNVTKDGDSYSL
RWETMKMRYEHIDHTFEIQYRKDTATWKDSKTETLQNAHSMALPALEPST
RYWARVRVRTSRTGYNGIWSEWSEARSWDTESVLPMWVLALIVIFLTTA
VLLALRFCGIYGYRLRRKWEEKIPNPSKSHLFQNGSAELWPPGSMSAFTS
GSPPHQGPWGSRFPELEGVFPVGFGDSEVSPLTIEDPKHVCDPPSGPDTTPA
ASDLPTEQPPSPQPGPPAASHTPEKQASSFDFNGPYLGPPHSRSLPDILGQP
EPPQEGGSQKSPPPGSLEYLCLPAGGQVQLVPLAQAMGPGQAVEVERRPSQ
GAAGSPSLESGGGPAPPALGPRVGGQDQKDSPVAIPMSSGDTEDPGVASGY
VSSADLVFTPNSGASSVSLVPSLGLPSDQTPSLCPGLASGPPGAPGPVKSGF
EGYVELPPIEGRSPRSPRNNPVPPEAKSPVLNPGERPADVSPTSPQPEGLL
VLQQVGDYCFLPGLGPGPLSLRSKPSSPGPGPEIKNLDQAFQVKKPPGQAV
PQVPVIQLFKALKQQDYLSLPPWEVNKPGEVC.

4. The nucleic acid of claim 3 wherein said polypeptide is defined by the amino acid sequence:

ERSLAGAEETIPLQTLRCYNDYTSHITCRWADTQDAQRLVNVTLIRRVNED
LLEPVSCDLSDDMPWSACPHPRCVPRRCVIPCQSFVVTDVDYFSFQPDRPL
GTRLTVTLTQHVQPPEPRDLQISTDQDHPLLTWSVALGSPQSHWLSFGDLEF
EVVYKRLQDSWEDAAILLSNTSQATLGPEHLMPSSTYVARVRTRLAPGSR
LSGRPSKWSPEVCWDSQPGDEAQPQNLECFFDGAAVLSCSWEVRKEVASSV
SFGLFYKPSPDAGEEECSPVLREGLGSLHTRHHCQIPVPDPATHGQYIVSVQ
PRRAEKHIKSSVNIQMAPPSLNVTKDGDSYSLRWETMKMRYEHIDHTFEI
QYRKDTATWKDSKTETLQNAHSMALPALEPSTRYWARVRVRTSRTGYNG
IWSEWSEARSWDTESVLPMWVLALIVIFLTTAVLLALRFCGIYGYRLRRK
WEEKIPNPSKSHLFQNGSAELWPPGSMSAFTSGSPPHQGPWGSRFPELEGV
FPVGFGDSEVSPLTIEDPKHVCDPPSGPDTTPAASDLPTEQPPSPQPGPPAAS
HTPEKQASSFDFNGPYLGPPHSRSLPDILGQPEPPQEGGSQKSPPPGSLEYLC
LPAGGQVQLVPLAQAMGPGQAVEVERRPSQGAAGSPSLESGGGPAPPALG
PRVGGQDQKDSPVAIPMSSGDTEDPGVASGYVSSADLVFTPNSGASSVSLV
PSLGLPSDQTPSLCPGLASGPPGAPGPVKSGFEGYVELPPIEGRSPRSPRNN
PVPPEAKSPVLNPGERPADVSPTSPQPEGLLVLQQVGDYCFLPGLGPGPLS
LRSKPSSPGPGPEIKNLDQAFQVKKPPGQAVPQVPVIQLFKALKQQDYLSL
PPWEVNKPGEVC.

* * * * *